US006921813B1

(12) United States Patent
Balganesh et al.

(10) Patent No.: US 6,921,813 B1
(45) Date of Patent: *Jul. 26, 2005

(54) DNA MOLECULES

(75) Inventors: Meenakshi Balganesh, Bangalore (IN); Umender Sharma, Bangalore (IN)

(73) Assignee: Astra Aktiebolag, Sodertalje (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/624,396

(22) PCT Filed: Mar. 12, 1996

(86) PCT No.: PCT/SE96/00319

§ 371 (c)(1),
(2), (4) Date: Apr. 4, 1996

(87) PCT Pub. No.: WO96/38478

PCT Pub. Date: Dec. 5, 1996

(30) Foreign Application Priority Data

| Mar. 13, 1995 | (IN) | 293/95 |
| May 30, 1995 | (SE) | 9501976 |
| Jul. 13, 1995 | (SE) | 9502596 |
| Sep. 19, 1995 | (SE) | 9503246 |

(51) Int. Cl.[7] .......................................... C07H 21/04
(52) U.S. Cl. ................ 536/23.2; 536/23.7; 536/24.1; 530/358; 435/4; 435/7.1; 435/69.2; 435/252.3; 435/233.3; 436/501

(58) Field of Search ............................... 536/23.1, 23.2, 536/23.7, 24.1; 435/252.3, 253.1, 69.2, 4, 7.1; 530/358; 436/501; 378/73

(56) References Cited

U.S. PATENT DOCUMENTS

| 5,573,910 A | * 11/1996 | Deretic et al. .................. 435/6 |
| 5,578,444 A | * 11/1996 | Edwards et al. ................ 435/6 |
| 5,783,386 A | 7/1998 | Jacobs, Jr. et al. |

OTHER PUBLICATIONS

Balganesh et al., J. Cell. Biochemistry, Supplementr 19B, Feb. 1995.*
Predich et al., Molecular Microbiology, vol. 15:355–366, Feb. 1995.*
Lehinger, Principles of Biochemistry, Worth Publishers, New York, p. 150, Jan. 1982.*
Doukhan, et al., Gene 165, 67–70 (1995).
Collins, et al., Proc. Natl. Acad. Sci. USA 92, 8036–8040 (1995).

* cited by examiner

Primary Examiner—Patrick J. Nolan
(74) Attorney, Agent, or Firm—White & Case LLP (57) ABSTRACT

The present invention provides novel nucleic acid molecules coding for sigma subunits of Mycobacterium tuberculosis RNA polymerase. It also relates to polypeptides, referred to as SigA and SigB, encoded by such nucleic acid molecules, as well as to vectors and host cells transformed with the said nucleic acid molecules. The invention further provides screening assays for compounds which inhibit the interaction between a sigma subunit and a core RNA polymerase.

18 Claims, 1 Drawing Sheet

DNA MOLECULES

This application is the National Stage of International Application No. PCT/SE96/00319, filed Mar. 12, 1996.

TECHNICAL FIELD

The present invention provides novel nucleic acid molecules coding for sigma subunits of *Mycobacterium tuberculosis* RNA polymerase. It also relates to polypeptides, referred to as SigA and SigB, encoded by such nucleic acid molecules, as well as to vectors and host cells transformed with the said nucleic acid molecules. The invention further provides screening assays for compounds which inhibit the interaction between a sigma subunit and a core RNA polymerase.

BACKGROUND ART

Transcription of genes to the corresponding RNA molecules is a complex process which is catalyzed by DNA dependent RNA polymerase, and involves many different protein factors. In eubacteria, the core RNA polymerase is composed of α, β, and β' subunits in the ratio 2:1:1. To direct RNA polymerase to promoters of specific genes to be transcribed, bacteria produce a variety of proteins, known as sigma (σ) factors, which interact with RNA polymerase to form an active holoenzyme. The resulting complexes are able to recognize and attach to selected nucleotide sequences in promoters.

Physical measurements have shown that the sigma subunit induces conformational transition upon binding to the core RNA polymerase. Binding of the sigma subunit to the core enzyme increases the binding constant of the core enzyme for DNA by several orders of magnitude (Chamberlin, M. J. (1974) Ann. Rev. Biochem. 43, 721-).

Characterisation of sigma subunits, identified and sequenced from various organisms, allows them to be classified into two broad categories; Group I and Group II. The Group I sigma has also been referred to as the $sigma^{70}$ class, or the "house keeping" sigma group. Sigma subunits belonging to this group recognise similar promoter sequences in the cell. These properties are reflected in certain regions of the proteins which are highly conserved between species.

Bacterial sigma factors do not have any homology with eukaryotic transcription factors, and are consequently a potential target for antibacterial compounds. Mutations in the sigma subunit, affecting its association and ability to confer DNA sequence specificity to the enzyme, are known to be lethal to the cell.

*Mycobacterium tuberculosis* is a major pulmonary pathogen which is characterized by its very slow growth rate. As a pathogen it gains access to alveolar macrophages where it multiplies within the phagosome, finally lysing the cells and being disseminated through the blood stream, not only to other areas of the lung, but also to extrapulmonary tissues. Thus the pathogen multiplies in at least two entirely different environments, which would involve the utilisation of different nutrients and a variety of possible host factors; a successful infection would thus involve the coordinated expression of new sets of genes. This regulation would resemble different physiological stages, as best exemplified by *Bacillus,* in which the expression of genes specific for different stages are transcribed by RNA polymerases associating with different sigma factors. This provides the possibility of targeting not only the house keeping sigma of *M. tuberculosis,* but also sigma subunits specific for the different stages of infection and dissemination.

BRIEF DESCRIPTION OF THE DRAWINGS

FIG. 1: Map of plasmid pARC 8175

FIG. 2: Map of plasmid pARC 8176

PURPOSE OF THE INVENTION

Since the association to a specific sigma subunit is essential for the specificity of RNA polymerase, this process of association is a suitable target for drug design. In order to identify compounds capable of inhibiting the said association process, the identification of the primary structures of sigma subunits is desirable.

It is thus the purpose of the invention to provide information on sequences and structure of sigma subunits, which information will enable the screening, identification and design of compounds competing with the sigma subunit for binding to the core RNA polymerase, which compounds may be developed into effective therapeutic agents.

Disclosure of the Invention

Throughout this description and in particular in the following examples, the terms "standard protocols" and "standard procedures", when used in the context of molecular cloning techniques, are to be understood as protocols and procedures found in an ordinary laboratory manual such as: Sambrook, J., Fritsch, E. F. and Maniatis, T. (1989) Molecular Cloning: A laboratory manual, 2nd Ed., Cold Spring Harbor Laboratory Press, Cold Spring Harbor, N.Y.

In a first aspect, this invention provides an isolated polypeptide which is a Group I sigma subunit of *Mycobacterium tuberculosis* RNA polymerase, or a functionally equivalent modified form thereof.

Preferred such polypeptides having amino acid sequences according to SEQ ID NO: 2 or 4 of the Sequence Listing have been obtained by recombinant DNA techniques and are hereinafter referred to as SigA and SigB polypeptides. However, it will be understood that the polypeptides according to the invention are not limited strictly to polypeptides with an amino acid sequence identical with SEQ ID NO: 2 or 4 in the Sequence Listing. Rather the invention additionally encompasses modified forms of these native polypeptides carrying modifications like substitutions, small deletions, insertions or inversions, which polypeptides nevertheless have substantially the biological activities of a *M. tuberculosis* sigma subunit. Such biological activities comprise the ability to associate with the core enzyme and/or confer the property of promoter sequence recognition and initiation of transcription. Included in the invention, consequently, are polypeptides, the amino acid sequences of which are at least 90% homologous, preferably at least 95% homologous, with the amino acid sequence shown as SEQ ID NO: 2 or 4 in the Sequence Listing.

In another aspect, the invention provides isolated and purified nucleic acid molecules which have a nucleotide sequence coding for a polypeptide of the invention e.g. the SigA or SigB polypeptide. In a preferred form of the invention, the nucleic acid molecules are DNA molecules which have a nucleotide sequence identical with SEQ ID NO: 1 or 3 of the Sequence Listing. However, the nucleic acid molecules according to the invention are not to be limited strictly to the DNA molecules with the sequence shown as SEQ ID NO: 1 or 3. Rather the invention encompasses nucleic acid molecules carrying modifications like substitutions, small deletions, insertions or inversions, which molecules nevertheless encode proteins having substantially the biochemical activity of the polypeptides according to the invention. Included in the invention, consequently, are DNA molecules, the nucleotide sequences of which are at least 90% homologous, preferably at least 95% homologous, with the nucleotide sequence shown as SEQ ID NO: 1 or 3 in the Sequence Listing.

Included in the invention are also DNA molecule whose nucleotide sequences are degenerate, because of the genetic code, to the nucleotide sequences shown as SEQ ID NO: 1 or 3. A sequential grouping of three nucleotides, a "codon", codes for one amino acid. Since there are 64 possible codons, but only 20 natural amino acids, most amino acids are coded for by more than one codon. This natural "degeneracy", or "redundancy", of the genetic code is well known in the art. It will thus be appreciated that the DNA sequence shown in the Sequence Listing is only an example within a large but definite group of DNA sequences which will encode the polypeptide as described above.

Included in the invention, consequently, are isolated nucleic acid molecule selected from:
(a) DNA molecules comprising a nucleotide sequence as shown in SEQ ID NO: 1 or SEQ ID NO: 3 encoding a Group I sigma subunit of *Mycobacterium tuberculosis* RNA polymerase;
(b) nucleic acid molecules comprising a nucleotide sequence capable of hybridizing to a nucleotide sequence complementary to the polypeptide coding region of a DNA molecule as defined in (a) and which codes for a polypeptide which is a Group I sigma subunit of *Mycobacterium tuberculosis* or a functionally equivalent modified form thereof; and
(c) nucleic acid molecules comprising a nucleic acid sequence which is degenerate, as a result of the genetic code, to a nucleotide sequence as defined in (a) or (b) and which codes for a polypeptide which is a Group I sigma subunit of *Mycobacterium tuberculosis* or a functionally equivalent modified form thereof.

The term "hybridizing to a nudeotide sequence" should be understood as hybridizing to a nucleotide sequence, or a specific part thereof, under stringent hybridization conditions which are known to a person skilled in the art.

A DNA molecule of the invention may be in the form of a vector, e.g. a replicable expression vector which carries and is capable of mediating the expression of a DNA molecule according to the invention. In the present context the term "replicable" means that the vector is able to replicate in a given type of host cell into which it has been introduced. Examples of vectors are viruses such as bacteriophages, cosmids, plasmids and other recombination vectors. Nucleic acid molecules are inserted into vector genomes by methods well known in the art. Vectors according to the invention can include the plasmid vector pARC 8175 (NCIMB 40738) which contains the coding sequence of the sigA gene, or pARC 8176 (NCIMB 40739) which contains the coding sequence of the sigB gene.

Included in the invention is also a host cell harbouring a vector according to the invention. Such a host cell can be a prokaryotic cell, a unicellular eukaryotic cell or a cell derived from a multicellular organism. The host cell can thus e.g. be a bacterial cell such as an *E. coli* cell; a cell from a yeast such as *Saccharomyces cervisiae* or *Pichia pastoris,* or a mammalian cell. The methods employed to effect introduction of the vector into the host cell are standard methods well known to a person familiar with recombinant DNA methods.

A further aspect of the invention is a process for production of a polypeptide of the invention, comprising culturing host cells transformed with an expression vector according to the invention under conditions whereby said polypeptide is produced, and recovering said polypeptide.

The medium used to grow the cells may be any conventional medium suitable for the purpose. A suitable vector may be any of the vectors described above, and an appropriate host cell may be any of the cell types listed above. The methods employed to construct the vector and effect introduction thereof into the host cell may be any methods known for such purposes within the field of recombinant DNA. The recombinant polypeptide expressed by the cells may be secreted, i.e. exported through the cell membrane, dependent on the type of cell and the composition of the vector.

If the polypeptide is produced intracellularly by the recombinant host, i.e. is not secreted by the cell, it may be recovered by standard procedures comprising cell disrupture by mechanical means, e.g. sonication or homogenization, or by enzymatic or chemical means followed by purification.

In order that the polypeptide be secreted, the DNA sequence encoding the polypeptide should be preceded by a sequence coding for a signal peptide, the presence of which ensures secretion of the polypeptide from the cells so that at least a significant proportion of the polypeptide expressed is secreted into the culture medium and recovered.

Another important aspect of the invention is a method of assaying for compounds which have the ability to inhibit the association of a sigma subunit to a *Mycobacterium tuberculosis* RNA polymerase, said method comprising the use of a recombinant SigA or SigB polypeptide or a nucleic acid molecule as defined above. Such a method will preferably comprise (i) contacting a compound to be tested for such inhibition ability with a SigA or SigB polypeptide as described above and a *Mycobacterium tuberculosis* core RNA polymerase; and (ii) detecting whether the polypeptide associates with the core RNA polymerase to form RNA polymerase holoenzyme. The term "core RNA polymerase" is to be understood as an RNA polymerase which comprises at least the $\alpha$, $\beta$, and $\beta'$ subunits, but not the sigma subunit. The term "RNA polymerase holoenzyme" is to be understood as an RNA polymerase comprising at least the $\alpha$, $\beta$, $\beta'$ and sigma subunits. If desirable, the sigma subunit polypeptide can be labelled, for example with a suitable radioactive molecule, e.g. $^{35}S$ or $^{125}I$.

Suitable methods for determining whether a sigma polypeptide has associated to core RNA polymerase are disclosed by Lesley et al. (Biochemistry 28, 7728–7734, 1989). Such a method may thus be based on the size difference between sigma polypeptides bound to core RNA polymerase, versus polypeptides not bound. This difference in size allows the two forms to be separated by chromatography, e.g. on a gel filtration column, such as a Waters Protein Pak® 300SW sizing column. The two forms eluted from the column may be detected and quantified by known methods, such as scintillation counting or SDS-PAGE followed by immunoblotting.

According to another method also described by Lesley et al. (supra), RNA polymerase holoenzyme is detected by immunoprecipitation using an antibody binding to RNA polymerase holoenzyme. Core RNA polymerase from an organism such as *E. coli, M. tuberculosis* or *M. smegmatis* can be allowed to react with a radiolabelled SigA or SigB polypeptide. The reaction mix is treated with a *Staphylococcus aureus* formalin-treated cell suspension, pretreated with an anti-RNA polymerase antibody. The cell suspension is washed to remove unbound proteins, resuspended in SDS-PAGE sample buffer and separated on SDS-PAGE. Bound SigA or SigB polypeptides are monitored by autoradiography followed by scintillation counting.

Another method of assaying for compounds which have the ability to inhibit sigma subunit-dependent transcription by a *Mycobacterium tuberculosis* RNA polymerase can comprise (i) contacting a compound to be tested for said inhibition ability with a polypeptide of the invention, a *Mycobacterium tuberculosis* core RNA polymerase, and a DNA having a coding sequence operably-linked to a promoter sequence capable of recognition by said core RNA polymerase when bound to said polypeptide, said contacting being carried out under conditions suitable for transcription of said coding sequence when *Mycobacterium tuberculosis* RNA polymerase is bound to said promoter; and (ii) detecting formation of mRNA corresponding to said coding sequence.

Such an assay is based on the fact that *E. coli* consensus promoter sequences are not transcribable by core RNA polymerase lacking the sigma subunit. However, addition of a sigma$^{70}$ protein will enable the complex to recognise specific promoters and initiate transcription. Screening of compounds which have the ability to inhibit sigma-dependent transcription can thus be performed, using DNA containing a suitable promoter as a template, by monitoring the formation of mRNA of specific lengths. Transcription can be monitored by measuring incorporation of $^3$H-UTP into TCA-precipitable counts (Ashok Kumar et al. (1994) J. Mol. Biol. 235, 405–413; Kajitani, M. and Ishihama, A. (1983) Nucleic Acids Res. 11, 671–686 and 3873–3888) and determining the length of the specific transcript. Compounds which are identified by such an assay can inhibit transcription by various mechanisms, such as (a) binding to a sigma protein and preventing its association with the core RNA polymerase; (b) binding to core RNA polymerase and sterically inhibiting the binding of a sigma protein; or (c) inhibiting intermediate steps involved in the initiation or elongation during transcription.

A further aspect of the invention is a method of determining the protein structure of a *Mycobacterium tuberculosis* RNA polymerase sigma subunit, characterised in that a SigA or SigB polypeptide is utilized in X-ray crystallography. The use of SigA or SigB polypeptide in crystallisation will facilitate a rational design, based on X-ray crystallography, of therapeutic compounds inhibiting interaction of a sigma$^{70}$ protein with the core RNA polymerase, alternatively inhibiting the binding of a sigma$^{70}$ protein, in association with a core RNA polymerase, to DNA during the course of gene transcription.

EXAMPLES

Examples 1

Identification of *M. tuberculosis* DNA Sequences Homologous to the Sigma$^{70}$ Gene 1.1. PCR Amplification of Putative Sigma$^{70}$ Homologues The following PCR primers were designed, based on the conserved amino acid sequences of sigma$^{45}$ (a sigma$^{70}$ homologue) of *Bacillus subtilis* and sigma$^{70}$ of *E. coli* (Gitt, M. A. et al. (1985) J. Biol. Chem. 260, 7178–7185):

Forward primer (SEQ ID NO: 5):

```
5'-AAG TTC AGC ACG TAC GCC ACG TGG TGG ATC-3'
            C           G   C
```

Reverse primer (SEQ ID NO: 6):

```
5'-CTT GGC CTC GAT CTG GCG GAT GCG CTC-3.
        C           C       C
```

The alternative nucleotides indicated at certain positions indicate that the primers are degenerate primers suitable for amplification of the unidentified gene.

Chromosomal DNA from *M. tuberculosis* H37RV (ATCC 27294) was prepared following standard protocols. PCR amplification of a DNA fragment of approximately 500 bp was carried out using the following conditions:

| Annealing: | +55° C. | 1 min |
| Denaturation: | +93° C. | 1 min |
| Extension: | +73° C. | 2 min |

1.2. Southern Hybridisation of *M. tuberculosis* DNA

Chromosomal DNA from *M. tuberculosis* H37RV (ATCC 27294), *M. tuberculosis* H37RA and *Mycobacterium smegmatis* was prepared following standard protocols and restricted with the restriction enzyme SalI. The DNA fragments were resolved on a 1% agarose gel by electrophoresis and transferred onto nylon membranes which were subjected to "Southern blotting" analysis following standard procedures. To detect homologous fragments, the membranes were probed with a radioactively labelled ~500 bp DNA fragment, generated by PCR as described above.

Analysis of the Southern hybridisation experiment revealed the presence of at least three hybridising fragments of approximately 4.2, 2.2 and 0.9 kb, respectively, in the SalI-digested DNA of both of the *M. tuberculosis* strains. In *M. smegmatis*, two hybridising fragments of 4.2 and 2.2 kb, respectively, were detected. It could be concluded that there were multiple DNA fragments with homology to the known sigma$^{70}$ genes.

Similar Southern hybridisation experiments, performed with four different clinical isolates of *M. tuberculosis*, revealed identical patterns, indicating the presence of similar genes also in other virulent isolates of *M. tuberculosis*.

Example 2

Cloning of Putative Sigma$^{70}$ Homologues 2.1. Cloning of *M. tuberculosis* sigA A lambda gt11 library (obtained from WHO) of the chromosomal DNA of *M. tuberculosis* Erdman strain was screened, using the 500 bp PCR probe as described above, following standard procedures. One lambda gt11 phage with a 4.7 kb EcoRI insert was identified and confirmed to hybridise with the PCR probe. Restriction analysis of this 4.7 kb insert revealed it to have an internal 2.2 kb SalI fragment which hybridised with the PCR probe.

Figure 1:
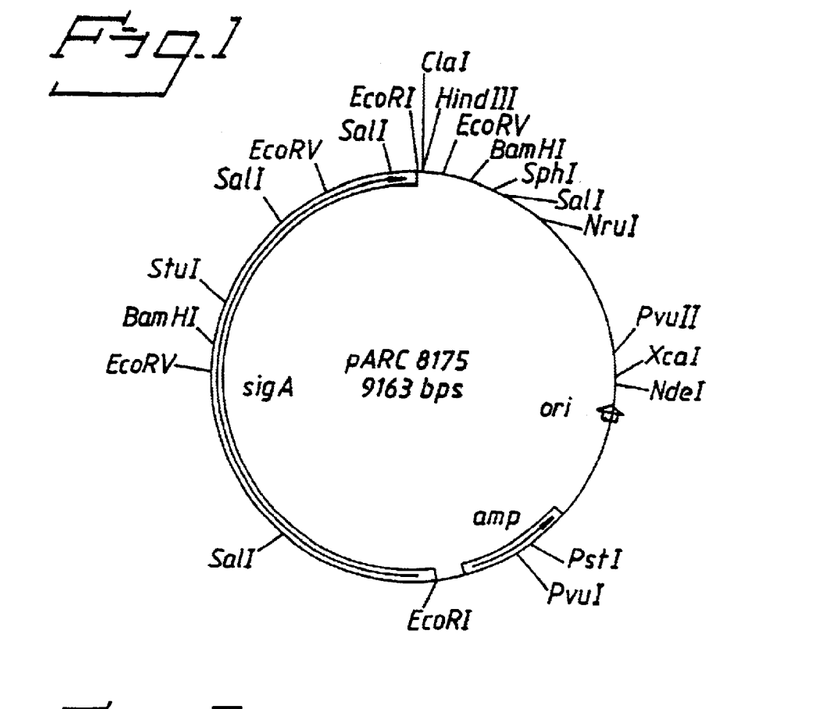

The 4.7 kb fragment was excised from the lambda gt 11 DNA by EcoRI restriction, and subcloned into the cloning vector pBR322, to obtain the recombinant plasmid pARC 8175 (FIG. 1) (NCIMB 40738).

The putative sigma$^{70}$ homologue on the 2.2 kb SalI fragment was designated *M. tuberculosis* sigA. The coding sequence of the sigA gene was found to have an internal SalI site, which could explain the hybridisation of the 0.9 kb fragment in the Southern experiments.

2.2. Cloning of *M. tuberculosis* sigB

Figure 2:
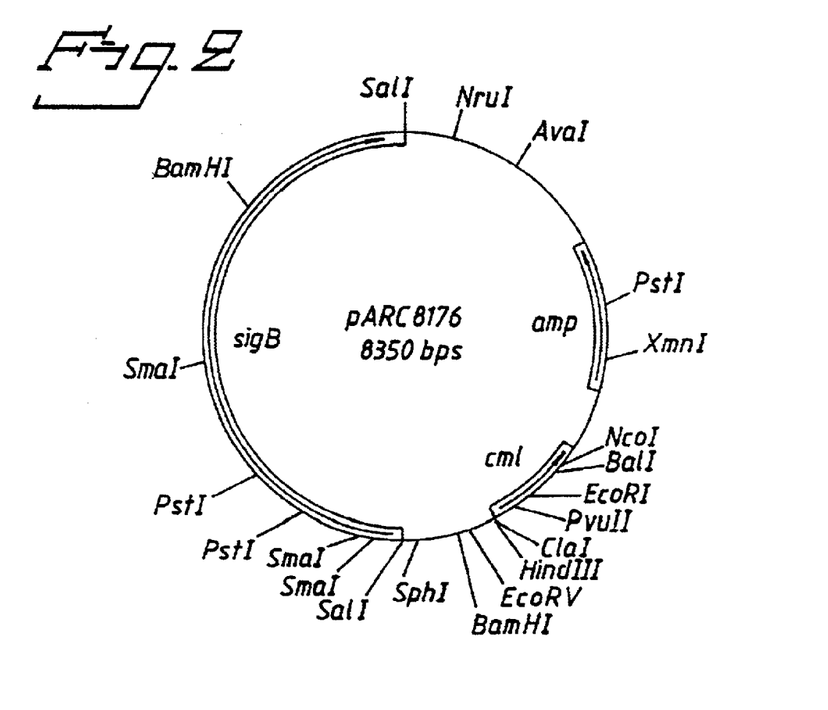

*M. tuberculosis* H37Rv DNA was restricted with SalI and the DNA fragments were resolved by preparative agarose gel electrophoresis. The agarose gel piece corresponding to the 4.0 to 5.0 kb size region was cut out, and the DNA from this gel piece was extracted following standard protocols. This DNA was ligated to the cloning vector pBR329 at its SalI site, and the ligated DNA was transformed into *E. coli* DH5α to obtain a sub-library. Transformants of this sub-library were identified by colony blotting, using the PCR-derived 500 bp probe, following standard protocols. Individual transformant colonies were analyzed for their plasmid profile. One of the recombinant plasmids retaining the expected plasmid size, was analyzed in detail by restriction mapping and was found to harbour the expected 4.2 kb SalI DNA fragment. This plasmid with the sigB gene on the 4.2 kb insert was designated pARC 8176 (FIG. 2) (NCIMB 40739).

Example 3

Nucleotide Sequence of M. tuberculosis sigA and sigB Genes 3.1. Nucleotide Sequence of sigA The EcoRV—EcoRI DNA fragment expected to encompass the entire sigA gene was subcloned into appropriate M13 vectors and both strands of the gene sequenced by the dideoxy method. The sequence obtained is shown as SEQ ID NO: 1 in the Sequence Listing. An open reading frame (ORF) of 1580 nucleotides (positions 70 to 1650 in SEQ ID NO: 1) coding for a protein of 526 amino adds was predicted from the DNA sequence. The N-terminal amino acid has been assigned tentatively based on the first GTG (initiation codon) of the ORF.

The derived amino acid sequence of the gene product SigA (SEQ ID NO: 2) showed 60% identity with the *E. coli* sigma$^{70}$ and 70% identity with the HrdB sequence of *Streptomyces coelicolor*. The overall anatomy of the SigA sequence is compatible with that seen among sigma$^{70}$ proteins of various organisms. This anatomy comprises a highly conserved C-terminal half, while the N-terminal half generally shows lesser homology. The two regions are linked by a stretch of amino acids which varies in length and is found to be generally unique for the protein. The SigA sequence has a similar structure, where the unconserved central stretch corresponds to amino acids 270 to 306 in SEQ ID NO: 2.

The N-terminal half has limited homology to *E. coli* sigma$^{70}$, but shows resemblance to that of the sigma$^{70}$ homologue HrdB of *S. coelicolor*. The highly conserved motifs of regions 3.1, 3.2, 4.1 and 4.2 of *S. coelicolor* which were proposed to be involved in DNA binding (Lonetto, M. et al. (1992) J. Bacteriol. 174, 3843–3849) are found to be nearly identical also in the *M. tuberculosis* SigA sequence. The N-terminal start of the protein has been tentatively assigned, based on homologous motifs of the *S. coelicolor* HrdB sequence.

The overall sequence similarity of the SigA and SigB amino acid sequences to known sigma$^{70}$ sequences suggests assignment of the *M. tuberculosis* SigA to the Group I sigma$^{70}$ proteins. However, SigA also shows distinct differences with known sigma$^{70}$ proteins, in particular a unique and lengthy N-terminal stretch of amino acids (positions 24 to 263 in SEQ ID NO: 2), which may be essential for the recognition and initiation of transcription from promoter sequences of *M. tuberculosis*.

3.2. Nucleotide Sequence of sigB

The nucleotide sequence of the sigB gene (SEQ ID NO: 3) encodes a protein of 323 amino acids (SEQ ID NO: 4). The N-terminal start of the protein has been tentatively identified based on the presence of the first methionine of the ORF. The ORF is thus estimated to start at position 325 and to end at 1293 in SEQ ID NO: 3. Alignment of the amino acid sequence of the sigB gene with other sigma$^{70}$ proteins places the sigB gene into the Group I family of sigma$^{70}$ proteins. The overall structure of the gene product SigB follows the same pattern as described for SigA. However, the SigB sequence has only 60% homology with the SigA sequence, as there are considerable differences not only within the unconserved regions of the protein, but also within the putative DNA binding regions of the sigB protein. These characteristics suggest that the SigB protein may play a distinct function in the physiology of the organism.

Example 4

Expression of sigA and sigB 4.1. Expression of *M. tuberculosis* sigA gene in *E. coli*

The N-terminal portion of the sigA gene was amplified by PCR using the following primers:

Forward primer (SEQ. ID NO: 7), comprising an NcoI site:

(SEQ. ID NO: 11)

Reverse primer (SEQ ID NO: 8):
5'-GTA CAG GCC AGC CTC GAT CCG CTT GGC-3'

(a) A fragment of approximately 750 bp was amplified from the sigA gene construct pARC 8175. The amplified product was restricted with NcoI and BamHI to obtain a 163 bp fragment.
(b) A 1400 bp DNA fragment was obtained by digestion of pARC 8175 with BamHI and EcoRV.
(c) The expression plasmid pET 8ck, which is a derivative of pET 8c (Studier, F.W et al. (1990) Methods Enzymol. 185, 61–89) in which the β-lactamase gene has been replaced by the gene conferring kanamycin resistance, was digested with NcoI and EcoRV and a fragment of approximately 4.2 kb was purified.

These three fragments (a), (b) and (c) were ligated by standard methods and the product was transformed into *E. coli* DH5α. Individual transformants were screened for the plasmid profile following standard protocols. The transformant was identified based on the expected plasmid size (approximately 6.35 kb) and restriction mapping of the plasmid. The recombinant plasmid harbouring the coding fragment of sigA was designated pARC 8171.

The plasmid pARC 8171 was transformed into the T$_7$ expression host *E. coli* BL21(DE3). Individual transformants were screened for the presence of the 6.35 kb plasmid and confirmed by restriction analysis. One of the transformants was grown at 37° C. and induced with 1 mM isopropyl-β-D- thiogalactopyranoside (IPTG) using standard protocols. A specific 90 kDa protein was induced on expression. Cells were harvested by low speed centrifugation and lysed by sonication in phosphate buffered saline, pH 7.4. The lysate was centrifugated at 100,000×g to fractionate into supernatant and pellet. The majority of the 70 kDa product obtained after induction with IPTG was present in the pellet fraction, indicating that the protein formed inclusion bodies.

For purifying the induced sigA gene product, the cell lysate as obtained above was clarified by centrifugation at 1000 rpm in a Beckman JA21 rotor for 15 min. The clarified supernatant was layered on a 15–60% sucrose gradient and centrifugated at 100,000×g for 60 min. The inclusion bodies sedimented as a pellet through the 60% sucrose cushion. This pellet was solubilised in 6 M guanidine hydrochloride which was removed by sequential dialysis against buffer containing decreasing concentrations of guanidine hydrochloride. The dialysate was 75% enriched for the SigA protein which was purified essentially following the protocol for purification of *E. coli* sigma$^{70}$ as described by Brokhov, S. and Goldfarb, A. (1993) Protein expression and purification, vol. 4, 503–511.

4.2. Expression of *M. tuberculosis* sigB Gene in *E. coli*

The sigB gene product was expressed and purified from inclusion bodies. The coding sequence of the sigB gene was amplified by PCR using the following primers:

Forward primer (SEQ. ID NO: 9), comprising an NcoI restriction site:

5'-TTTC ATG GCC GAT GCA CCC ACA AGG GCC-3'
      M   A   D   A   P   T   R   A (SEQ. ID NO: 12)

Reverse primer (SEQ ID NO: 10), comprising an EcoRI restriction site:
5'-CTT GAA TTC AGC TGG CGT ACG ACC GCA-3'

The amplified 920 bp fragment was digested with EcoRI and NcoI and ligated to the EcoRI- and NcoI-digested pRSET B (Kroll et al. (1993) DNA and Cell Biology 12, 441). The ligation mix was transformed into *E. coli* DH5α. Individual transformants were screened for plasmid profile and restriction analysis. The recombinant plasmid having the expected plasmid profile was designated pARC 8193.

*E. coli* DH5α harbouring pARC8193 was cultured in LB containing 50 μg/ml ampicillin till reaching an OD of 0.5, and induced with 1 mM IPTG at 37° C., following standard protocols. The induced SigB protein was obtained as inclusion bodies which were denatured and renatured following the same protocol as described for the SigA protein. The purified SigB protein was >90% homogenous and suitable for transcription assays.

Deposit of Microorganisms

The following plasmids have been deposited under the Budapest Treaty at the National Collections of Industrial and Marine Bacteria (NCIMB), Aberdeen, Scotland, UK.

| Plasmid | Accession No. | Date of deposit |
| --- | --- | --- |
| pARC 8175 | NCIMB 40738 | Jun. 15, 1995 |
| pARC 8176 | NCIMB 40739 | Jun. 15, 1995 |

---

What is claimed is:

1. An isolated polypeptide which comprises an amino acid sequence at least 95% homologous to the amino acid sequence shown in SEQ ID NO: 4 in the Sequence Listing, which polypeptide has biological activities comprising the ability to associate with the core *Mycobacterium tuberculosis* RNA polymerase and/or the ability to confer the property of promoter sequence recognition and initiation of transcription.

2. An isolated nucleic acid molecule selected from the group consisting of: (a) a DNA molecule comprising a nucleotide sequence as shown in SEQ ID NO: 3 encoding a polypeptide comprising an amino acid sequence as shown in SEQ ID NO: 4; and (b) a nucleic acid molecule comprising a nucleic acid sequence which is degenerate, as a result of the genetic code, to a nucleotide sequence as defined in (a) above.

3. An isolated nucleic acid molecule which comprises a nucleotide sequence coding for a polypeptide according to claim 1.

4. A vector which comprises a nucleic acid molecule according to claim 2 or 3.

5. A vector according to claim 4 which is an expression vector capable of mediating the expression of a polypeptide encoded by the nucleic acid molecule which is a component of said vector.

6. A vector according to claim 4 which is an expression vector capable of mediating the expression of a polypeptide which comprises an amino acid sequence at least 95% homologous to the amino acid sequence shown in SEQ ID NO: 4 in the Sequence Listing.

7. A vector which is the plasmid vector pARC 8176 (NCIMB 40739).

8. A host cell harboring a vector according to claim 4.

9. A host cell harboring a vector according to claim 7.

10. A host cell harboring a vector according to claim 5.

11. A host cell harboring a vector according to claim 6.

12. A process for production of a polypeptide comprising an amino acid sequence at least 95% homologous to that shown in SEQ ID NO: 4, which comprises (i) culturing a host cell harboring and transformed with an expression vector according to claim 5 under conditions whereby the polypeptide is produced and (ii) recovering the polypeptide.

13. A process for production of a polypeptide which comprises an amino acid sequence at least 95% homologous to the amino acid sequence shown in SEQ ID NO: 4 in the Sequence Listing, which comprises (i) culturing a host cell harboring and transformed with an expression vector according to claim 6 under conditions whereby said polypeptide is produced; and (ii) recovering said polypeptide.

14. A method of assaying for compounds which have the ability to inhibit the association of a sigma subunit with a *Mycobacterium tuberculosis* core RNA polymerase, which comprises (i) contacting a compound to be tested for said inhibition ability with a polypeptide according to claim 1 and a *Mycobacterium tuberculosis* core RNA polymerase; and (ii) detecting whether the polypeptide associates with the core RNA polymerase holoenzyme.

15. A method according to claim 14 wherein polypeptides which are associated with core RNA polymerase and/or polypeptides which are not associated with core RNA polymerase are detected by chromatography.

16. A method according to claim 14 wherein RNA polymerase holoenzyme is detected by immunoprecipitation, using an antibody binding to RNA polymerase holoenzyme.

17. A method of assaying for compounds which have the ability to inhibit sigma subunit-dependent transcription by a *Mycobacterium tuberculosis* RNA polymerase, which comprises (i) contacting a compound to be tested for said inhibition ability with a polypeptide according to claim 1, a *Mycobacterium tuberculosis* core RNA polymerase and a DNA molecule having a coding sequence operably linked to a promoter sequence capable of recognition by said core RNA polymerase when bound to said polypeptide, said contacting being carried out under conditions suitable for transcription of said coding sequence when *Mycobacterium tuberculosis* RNA polymerase is bound to said promoter; and (ii) detecting formation of mRNA corresponding to said coding sequence.

18. A method according to claim 17 which employs gel filtration chromatography.

* * * * *

UNITED STATES PATENT AND TRADEMARK OFFICE
CERTIFICATE OF CORRECTION

PATENT NO. : 6,921,813 B1 Page 1 of 1
APPLICATION NO. : 08/624396
DATED : July 26, 2005
INVENTOR(S) : Balganesh et al.

It is certified that error appears in the above-identified patent and that said Letters Patent is hereby corrected as shown below:

<u>Col. 26, line 38</u>
"claim 17" should read --claim 15--.

Signed and Sealed this

Eighteenth Day of July, 2006

JON W. DUDAS
*Director of the United States Patent and Trademark Office*

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 1724 base pairs
      (B) TYPE: nucleic acid
      (C) STRANDEDNESS: both
      (D) TOPOLOGY: linear    (vi) ORIGINAL SOURCE:
      (A) ORGANISM: Mycobacterium tuberculosis
      (B) STRAIN: Erdman strain    (vii) IMMEDIATE SOURCE:
      (B) CLONE: pARC 8175

(ix) FEATURE:
      (A) NAME/KEY: CDS
      (B) LOCATION: 70..1653

(xi) SEQUENCE DESCRIPTION: SEQ ID NO: 1:

```
AACTAGCAGA CACTTTCGGT TACGCACGCC CAGACCCAAC CGGAAGTGAG TAACGACCGA        60

AGGGTGTAT GTG GCA GCG ACC AAA GCA AGC ACG GCG ACC GAT GAG CCG          108
          Val Ala Ala Thr Lys Ala Ser Thr Ala Thr Asp Glu Pro
            1               5                  10

GTA AAA CGC ACC GCC ACC AAG TCG CCC GCG GCT TCC GCG TCC GGG GCC        156
Val Lys Arg Thr Ala Thr Lys Ser Pro Ala Ala Ser Ala Ser Gly Ala
     15                  20                  25

AAG ACC GGC GCC AAG CGA ACA GCG GCG AAG TCC GCT AGT GGC TCC CCA        204
Lys Thr Gly Ala Lys Arg Thr Ala Ala Lys Ser Ala Ser Gly Ser Pro
 30                  35                  40                  45

CCC GCG AAG CGG GCT ACC AAG CCC GCG GCC CGG TCC GTC AAG CCC GCC        252
Pro Ala Lys Arg Ala Thr Lys Pro Ala Ala Arg Ser Val Lys Pro Ala
                 50                  55                  60

TCG GCA CCC CAG GAC ACT ACG ACC AGC ACC ATC CCG AAA AGG AAG ACC        300
Ser Ala Pro Gln Asp Thr Thr Thr Ser Thr Ile Pro Lys Arg Lys Thr
             65                  70                  75

CGC GCC GCG GCC AAA TCC GCC GCC GCG AAG GCA CCG TCG GCC CGC GGC        348
```

```
                                                                -continued

Arg Ala Ala Ala Lys Ser Ala Ala Lys Ala Pro Ser Ala Arg Gly
         80              85              90

CAC GCG ACC AAG CCA CGG GCG CCC AAG GAT GCC CAG CAC GAA GCC GCA              396
His Ala Thr Lys Pro Arg Ala Pro Lys Asp Ala Gln His Glu Ala Ala
         95              100             105

ACG GAT CCC GAG GAC GCC CTG GAC TCC GTC GAG GAG CTC GAC GCT GAA              444
Thr Asp Pro Glu Asp Ala Leu Asp Ser Val Glu Glu Leu Asp Ala Glu
110             115             120                             125

CCA GAC CTC GAC GTC GAG CCC GGC GAG GAC CTC GAC CTT GAC GCC GCC              492
Pro Asp Leu Asp Val Glu Pro Gly Glu Asp Leu Asp Leu Asp Ala Ala
                130             135                 140

GAC CTC AAC CTC GAT GAC CTC GAG GAC GAC GTG GCG CCG GAC GCC GAC              540
Asp Leu Asn Leu Asp Asp Leu Glu Asp Asp Val Ala Pro Asp Ala Asp
            145             150                 155

GAC GAC CTC GAC TCG GGC GAC GAC GAA GAC CAC GAA GAC CTC GAA GCT              588
Asp Asp Leu Asp Ser Gly Asp Asp Glu Asp His Glu Asp Leu Glu Ala
        160             165             170

GAG GCG GCC GTC GCG CCC GGC CAG ACC GCC GAT GAC GAC GAG GAG ATC              636
Glu Ala Ala Val Ala Pro Gly Gln Thr Ala Asp Asp Asp Glu Glu Ile
    175             180             185

GCT GAA CCC ACC GAA AAG GAC AAG GCC TCC GGT GAT TTC GTC TGG GAT              684
Ala Glu Pro Thr Glu Lys Asp Lys Ala Ser Gly Asp Phe Val Trp Asp
190             195             200                             205

GAA GAC GAG TCG GAG GCC CTG CGT CAA GCA CGC AAG GAC GCC GAA CTC              732
Glu Asp Glu Ser Glu Ala Leu Arg Gln Ala Arg Lys Asp Ala Glu Leu
                210             215                 220

ACC GCA TCC GCC GAC TCG GTT CGC GCC TAC CTC AAA CAG ATC GGC AAG              780
Thr Ala Ser Ala Asp Ser Val Arg Ala Tyr Leu Lys Gln Ile Gly Lys
            225             230                 235

GTA GCG CTG CTC AAC GCC GAG GAA GAG GTC GAG CTA GCC AAG CGG ATC              828
Val Ala Leu Leu Asn Ala Glu Glu Glu Val Glu Leu Ala Lys Arg Ile
        240             245             250

GAG GCT GGC CTG TAC GCC ACG CAG CTG ATG ACC GAG CTT AGC GAG CGC              876
Glu Ala Gly Leu Tyr Ala Thr Gln Leu Met Thr Glu Leu Ser Glu Arg
    255             260             265

GGC GAA AAG CTG CCT GCC GCC CAG CGC CGC GAC ATG ATG TGG ATC TGC              924
Gly Glu Lys Leu Pro Ala Ala Gln Arg Arg Asp Met Met Trp Ile Cys
270             275             280                             285

CGC GAC GGC GAT CGC GCG AAA AAC CAT CTG CTG GAA GCC AAC CTG CGC              972
Arg Asp Gly Asp Arg Ala Lys Asn His Leu Leu Glu Ala Asn Leu Arg
                290             295                 300

CTG GTG GTT TCG CTA GCC AAG CGC TAC ACC GGC CGG GGC ATG GCG TTT             1020
Leu Val Val Ser Leu Ala Lys Arg Tyr Thr Gly Arg Gly Met Ala Phe
            305             310                 315

CTC GAC CTG ATC CAG GAA GGC AAC CTG GGG CTG ATC CGC GCG GTG GAG             1068
Leu Asp Leu Ile Gln Glu Gly Asn Leu Gly Leu Ile Arg Ala Val Glu
        320             325             330

AAG TTC GAC TAC ACC AAG GGG TAC AAG TTC TCC ACC TAC GCT ACG TGG             1116
Lys Phe Asp Tyr Thr Lys Gly Tyr Lys Phe Ser Thr Tyr Ala Thr Trp
    335             340             345

TGG ATT CGC CAG GCC ATC ACC CGC GCC ATG GCC GAC CAG GCC CGC ACC             1164
Trp Ile Arg Gln Ala Ile Thr Arg Ala Met Ala Asp Gln Ala Arg Thr
350             355             360                             365

ATC CGC ATC CCG GTG CAC ATG GTC GAG GTG ATC AAC AAG CTG GGC CGC             1212
Ile Arg Ile Pro Val His Met Val Glu Val Ile Asn Lys Leu Gly Arg
                370             375                 380

ATT CAA CGC GAG CTG CTG CAG GAC CTG GGC CGC GAG CCC ACG CCC GAG             1260
Ile Gln Arg Glu Leu Leu Gln Asp Leu Gly Arg Glu Pro Thr Pro Glu
            385             390                 395
```

```
GAG CTG GCC AAA GAG ATG GAC ATC ACC CCG GAG AAG GTG CTG GAA ATC       1308
Glu Leu Ala Lys Glu Met Asp Ile Thr Pro Glu Lys Val Leu Glu Ile
        400                 405                 410

CAG CAA TAC GCC CGC GAG CCG ATC TCG TTG GAC CAG ACC ATC GGC GAC       1356
Gln Gln Tyr Ala Arg Glu Pro Ile Ser Leu Asp Gln Thr Ile Gly Asp
    415                 420                 425

GAG GGC GAC AGC CAG CTT GGC GAT TTC ATC GAA GAC AGC GAG GCG GTG       1404
Glu Gly Asp Ser Gln Leu Gly Asp Phe Ile Glu Asp Ser Glu Ala Val
430                 435                 440                 445

GTG GCC GTC GAC GCG GTG TCC TTC ACT TTG CTG CAG GAT CAA CTG CAG       1452
Val Ala Val Asp Ala Val Ser Phe Thr Leu Leu Gln Asp Gln Leu Gln
            450                 455                 460

TCG GTG CTG GAC ACG CTC TCC GAG CGT GAG GCG GGC GTG GTG CGG CTA       1500
Ser Val Leu Asp Thr Leu Ser Glu Arg Glu Ala Gly Val Val Arg Leu
        465                 470                 475

CGC TTC GGC CTT ACC GAC GGC CAG CCG CGC ACC CTT GAC GAG ATC GGC       1548
Arg Phe Gly Leu Thr Asp Gly Gln Pro Arg Thr Leu Asp Glu Ile Gly
    480                 485                 490

CAG GTC TAC GGC GTG ACC CGG GAA CGC ATC CGC CAG ATC GAA TCC AAG       1596
Gln Val Tyr Gly Val Thr Arg Glu Arg Ile Arg Gln Ile Glu Ser Lys
495                 500                 505

ACT ATG TCG AAG TTG CGC CAT CCG AGC CGC TCA CAG GTC CTG CGC GAC       1644
Thr Met Ser Lys Leu Arg His Pro Ser Arg Ser Gln Val Leu Arg Asp
510                 515                 520                 525

TAC CTG GAC TGAGAGCGCC CGCCGAGGCG ACCAACGTAG CACGTGAGCC               1693
Tyr Leu Asp

CCCAGCAGCT AGCCGCACCA TGGTCTCGTC C                                    1724

(2) INFORMATION FOR SEQ ID NO: 2:

(i) SEQUENCE CHARACTERISTICS:
        (A) LENGTH: 528 amino acids
        (B) TYPE: amino acid
        (D) TOPOLOGY: linear (ii) MOLECULE TYPE: protein (xi) SEQUENCE DESCRIPTION: SEQ ID NO: 2:

Val Ala Ala Thr Lys Ala Ser Thr Ala Thr Asp Glu Pro Val Lys Arg
1               5                   10                  15

Thr Ala Thr Lys Ser Pro Ala Ala Ser Ala Ser Gly Ala Lys Thr Gly
                20                  25                  30

Ala Lys Arg Thr Ala Ala Lys Ser Ala Ser Gly Ser Pro Pro Ala Lys
            35                  40                  45

Arg Ala Thr Lys Pro Ala Ala Arg Ser Val Lys Pro Ala Ser Ala Pro
        50                  55                  60

Gln Asp Thr Thr Thr Ser Thr Ile Pro Lys Arg Lys Thr Arg Ala Ala
65                  70                  75                  80

Ala Lys Ser Ala Ala Ala Lys Ala Pro Ser Ala Arg Gly His Ala Thr
                85                  90                  95

Lys Pro Arg Ala Pro Lys Asp Ala Gln His Glu Ala Ala Thr Asp Pro
            100                 105                 110

Glu Asp Ala Leu Asp Ser Val Glu Glu Leu Asp Ala Glu Pro Asp Leu
        115                 120                 125

Asp Val Glu Pro Gly Glu Asp Leu Asp Leu Asp Ala Ala Asp Leu Asn
    130                 135                 140

Leu Asp Asp Leu Glu Asp Asp Val Ala Pro Asp Ala Asp Asp Asp Leu
145                 150                 155                 160
```

-continued

Asp Ser Gly Asp Asp Glu Asp His Glu Asp Leu Glu Ala Glu Ala Ala
            165                 170                 175

Val Ala Pro Gly Gln Thr Ala Asp Asp Glu Glu Ile Ala Glu Pro
            180                 185                 190

Thr Glu Lys Asp Lys Ala Ser Gly Asp Phe Val Trp Asp Glu Asp Glu
            195                 200                 205

Ser Glu Ala Leu Arg Gln Ala Arg Lys Asp Ala Glu Leu Thr Ala Ser
            210                 215                 220

Ala Asp Ser Val Arg Ala Tyr Leu Lys Gln Ile Gly Lys Val Ala Leu
225                 230                 235                 240

Leu Asn Ala Glu Glu Val Glu Leu Ala Lys Arg Ile Glu Ala Gly
            245                 250                 255

Leu Tyr Ala Thr Gln Leu Met Thr Glu Leu Ser Glu Arg Gly Glu Lys
            260                 265                 270

Leu Pro Ala Ala Gln Arg Arg Asp Met Met Trp Ile Cys Arg Asp Gly
            275                 280                 285

Asp Arg Ala Lys Asn His Leu Leu Glu Ala Asn Leu Arg Leu Val Val
            290                 295                 300

Ser Leu Ala Lys Arg Tyr Thr Gly Arg Gly Met Ala Phe Leu Asp Leu
305                 310                 315                 320

Ile Gln Glu Gly Asn Leu Gly Leu Ile Arg Ala Val Glu Lys Phe Asp
            325                 330                 335

Tyr Thr Lys Gly Tyr Lys Phe Ser Thr Tyr Ala Thr Trp Trp Ile Arg
            340                 345                 350

Gln Ala Ile Thr Arg Ala Met Ala Asp Gln Ala Arg Thr Ile Arg Ile
            355                 360                 365

Pro Val His Met Val Glu Val Ile Asn Lys Leu Gly Arg Ile Gln Arg
            370                 375                 380

Glu Leu Leu Gln Asp Leu Gly Arg Glu Pro Thr Pro Glu Glu Leu Ala
385                 390                 395                 400

Lys Glu Met Asp Ile Thr Pro Glu Lys Val Leu Glu Ile Gln Gln Tyr
            405                 410                 415

Ala Arg Glu Pro Ile Ser Leu Asp Gln Thr Ile Gly Asp Glu Gly Asp
            420                 425                 430

Ser Gln Leu Gly Asp Phe Ile Glu Asp Ser Glu Ala Val Val Ala Val
            435                 440                 445

Asp Ala Val Ser Phe Thr Leu Leu Gln Asp Gln Leu Gln Ser Val Leu
450                 455                 460

Asp Thr Leu Ser Glu Arg Glu Ala Gly Val Val Arg Leu Arg Phe Gly
465                 470                 475                 480

Leu Thr Asp Gly Gln Pro Arg Thr Leu Asp Glu Ile Gly Gln Val Tyr
            485                 490                 495

Gly Val Thr Arg Glu Arg Ile Arg Gln Ile Glu Ser Lys Thr Met Ser
            500                 505                 510

Lys Leu Arg His Pro Ser Arg Ser Gln Val Leu Arg Asp Tyr Leu Asp
            515                 520                 525

(2) INFORMATION FOR SEQ ID NO: 3:

(i) SEQUENCE CHARACTERISTICS:
        (A) LENGTH: 1508 base pairs
        (B) TYPE: nucleic acid
        (C) STRANDEDNESS: both
        (D) TOPOLOGY: linear (vi) ORIGINAL SOURCE:

-continued

```
        (A) ORGANISM: Mycobacterium tuberculosis
        (C) INDIVIDUAL ISOLATE: atcc27294

(vii) IMMEDIATE SOURCE:
        (B) CLONE: pARC 8176

(ix) FEATURE:
        (A) NAME/KEY: CDS
        (B) LOCATION: 325..1293

(xi) SEQUENCE DESCRIPTION: SEQ ID NO: 3:

ACCAGCCCGA CGACCGACGA ACCCCGCCGC TTCGACGTGC CCAGCCGGCG CATCCCGCTG      60

TTCCCGACCG CGAACGGCCC GCACTCGAGC CGACGGCGAC AGCCGGCAAG AAGCGGTCAG     120

CCCGCGGGGA TTCGCCGACC ACGGTTAGCC GTCTGTTGGC CGGCGTTCCG GGTTGTCGCC     180

ACTGGCCACA CTTCTCAGGA CTTTCTCAGG TCTTCGGCAG ATTCCTGCAC GTCACAGGGC     240

GTCAGATCAC TGCTGGGTGG GAACTCAAAG TCCGGCTTTG TCGTTAAACC CTGACAGTGC     300

AAGCCGATCG GGGAACGGCT CGCT ATG GCC GAT GCA CCC ACA AGG GCC ACC       351
                           Met Ala Asp Ala Pro Thr Arg Ala Thr
                               530                 535

ACA AGC CGG GTT GAC ACA GAT CTG GAT GCT CAA AGC CCC GCG GCG GAC       399
Thr Ser Arg Val Asp Thr Asp Leu Asp Ala Gln Ser Pro Ala Ala Asp
        540                 545                 550

CTC GTG CGC GTC TAT CTG AAC GGC ATC GGC AAG ACG GCG TTG CTC AAC       447
Leu Val Arg Val Tyr Leu Asn Gly Ile Gly Lys Thr Ala Leu Leu Asn
    555                 560                 565

GCG GCG GAT GAA GTC GAA CTG GCC AAG CGC ATA GAA GCC GGG TTG TAT       495
Ala Ala Asp Glu Val Glu Leu Ala Lys Arg Ile Glu Ala Gly Leu Tyr
570                 575                 580                 585

GCC GAG CAT CTG CTG GAA ACC CGG AAG CGC CTC GGC GAG AAC CGA AAA       543
Ala Glu His Leu Leu Glu Thr Arg Lys Arg Leu Gly Glu Asn Arg Lys
                590                 595                 600

CGC GAC CTG GCG GCC GTG GTG CGT GAT GGC GAG GCC GCC CGC CGC CAC       591
Arg Asp Leu Ala Ala Val Val Arg Asp Gly Glu Ala Ala Arg Arg His
            605                 610                 615

CTG CTG GAA GCA AAC CTG CGG CTG GTG GTA TCG CTG GCC AAG CGC TAC       639
Leu Leu Glu Ala Asn Leu Arg Leu Val Val Ser Leu Ala Lys Arg Tyr
        620                 625                 630

ACG GGT CGG GGC ATG CCG TTG CTG GAC CTC ATC CAG GAG GGC AAC CTG       687
Thr Gly Arg Gly Met Pro Leu Leu Asp Leu Ile Gln Glu Gly Asn Leu
    635                 640                 645

GGT CTG ATC CGA GCG ATG GAG AAG TTC GAC TAC ACA AAG GGA TTC AAG       735
Gly Leu Ile Arg Ala Met Glu Lys Phe Asp Tyr Thr Lys Gly Phe Lys
650                 655                 660                 665

TTC TCA ACG TAT GCC ACG TGG TGG ATC CGC CAG GCC ATC ACC CGC GGA       783
Phe Ser Thr Tyr Ala Thr Trp Trp Ile Arg Gln Ala Ile Thr Arg Gly
                670                 675                 680

ATG GCC GAC CAG AGC CGC ACC ATC CGC CTG CCC GTA CAC CTG GTT GAG       831
Met Ala Asp Gln Ser Arg Thr Ile Arg Leu Pro Val His Leu Val Glu
            685                 690                 695

CAG GTC AAC AAG CTG GCG CGG ATC AAG CGG GAG ATG CAC CAG CAT CTG       879
Gln Val Asn Lys Leu Ala Arg Ile Lys Arg Glu Met His Gln His Leu
        700                 705                 710

GGT CGC GAA CGC ACC GAT GAG GAG CTC GCC GCC GAA TCC GGC ATT CCA       927
Gly Arg Glu Arg Thr Asp Glu Glu Leu Ala Ala Glu Ser Gly Ile Pro
    715                 720                 725

ATC GAC AAG ATC AAC GAC CTG CTG GAA CAC AGT CGC GAC CCG GTG AGT       975
Ile Asp Lys Ile Asn Asp Leu Leu Glu His Ser Arg Asp Pro Val Ser
730                 735                 740                 745

CTG GAT ATG CCG GTC GGC TCC GAG GAG GAG GCC CCT TTG GGC GAT TTC      1023
```

```
                                                    -continued

ATC GAG GAC GCC GAA GCC ATG TCC GCG GAG AAC GCG GTC ATC GCC GAA    1071
Ile Glu Asp Ala Glu Ala Met Ser Ala Glu Asn Ala Val Ile Ala Glu
            765                 770                 775

CTG TTA CAC ACC GAC ATC CGC AGC GTG CTG GCC ACT CTC GAC GAG CGT    1119
Leu Leu His Thr Asp Ile Arg Ser Val Leu Ala Thr Leu Asp Glu Arg
            780                 785                 790

GAC GAC CAG GTG ATC CGG CTG CGC TTC GGC CTG GAT GAC GGC CAA CCA    1167
Asp Asp Gln Val Ile Arg Leu Arg Phe Gly Leu Asp Asp Gly Gln Pro
    795                 800                 805

CGC ACC CTG GAT CAA ATC GGC AAA CTA TTC GGG CTG TCC CGT GAG CGG    1215
Arg Thr Leu Asp Gln Ile Gly Lys Leu Phe Gly Leu Ser Arg Glu Arg
810                 815                 820                 825

GTT CGT CAG ATC GAG CGC GAC GTG ATG AGT AAG CTG CGG CAC GGT GAG    1263
Val Arg Gln Ile Glu Arg Asp Val Met Ser Lys Leu Arg His Gly Glu
                830                 835                 840

CGG GCG GAT CGG CTG CGG TCG TAC GCC AGC TGAAGCTGGA CATCCTGAGC      1313
Arg Ala Asp Arg Leu Arg Ser Tyr Ala Ser
            845                 850

CAGGTAGCAG ACGGTATGCC CGCCGCGCCA GCATAGCCTG CGGTGGGGCG GCGGGCAACC   1373

ATTTTCGCAG CTGGCCAAGT GTAGACTCAG CTGCAATGGA GGGTGCTGAA TGAACGAGTT   1433

GGTTGATACC ACCGAGATGT ACCTGCGGAC CATCTACGAC CTCGAGGAAG AGGGCGTGAC   1493

GCACTGCGTG CCGGA                                                   1508

(2) INFORMATION FOR SEQ ID NO: 4:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO: 4:

Met Ala Asp Ala Pro Thr Arg Ala Thr Thr Ser Arg Val Asp Thr Asp
  1               5                  10                  15

Leu Asp Ala Gln Ser Pro Ala Ala Asp Leu Val Arg Val Tyr Leu Asn
                 20                  25                  30

Gly Ile Gly Lys Thr Ala Leu Leu Asn Ala Ala Asp Glu Val Glu Leu
             35                  40                  45

Ala Lys Arg Ile Glu Ala Gly Leu Tyr Ala Glu His Leu Leu Glu Thr
 50                  55                  60

Arg Lys Arg Leu Gly Glu Asn Arg Lys Arg Asp Leu Ala Ala Val Val
 65                  70                  75                  80

Arg Asp Gly Glu Ala Ala Arg Arg His Leu Leu Glu Ala Asn Leu Arg
                 85                  90                  95

Leu Val Val Ser Leu Ala Lys Arg Tyr Thr Gly Arg Gly Met Pro Leu
                100                 105                 110

Leu Asp Leu Ile Gln Glu Gly Asn Leu Gly Leu Ile Arg Ala Met Glu
            115                 120                 125

Lys Phe Asp Tyr Thr Lys Gly Phe Lys Phe Ser Thr Tyr Ala Thr Trp
130                 135                 140

Trp Ile Arg Gln Ala Ile Thr Arg Gly Met Ala Asp Gln Ser Arg Thr
145                 150                 155                 160

Ile Arg Leu Pro Val His Leu Val Glu Gln Val Asn Lys Leu Ala Arg
                165                 170                 175
```

```
Ile Lys Arg Glu Met His Gln His Leu Gly Arg Glu Arg Thr Asp Glu
            180                 185                 190

Glu Leu Ala Ala Glu Ser Gly Ile Pro Ile Asp Lys Ile Asn Asp Leu
            195                 200                 205

Leu Glu His Ser Arg Asp Pro Val Ser Leu Asp Met Pro Val Gly Ser
            210                 215                 220

Glu Glu Glu Ala Pro Leu Gly Asp Phe Ile Glu Asp Ala Glu Ala Met
225                 230                 235                 240

Ser Ala Glu Asn Ala Val Ile Ala Glu Leu Leu His Thr Asp Ile Arg
                245                 250                 255

Ser Val Leu Ala Thr Leu Asp Glu Arg Asp Asp Gln Val Ile Arg Leu
            260                 265                 270

Arg Phe Gly Leu Asp Asp Gly Gln Pro Arg Thr Leu Asp Gln Ile Gly
            275                 280                 285

Lys Leu Phe Gly Leu Ser Arg Glu Arg Val Arg Gln Ile Glu Arg Asp
            290                 295                 300

Val Met Ser Lys Leu Arg His Gly Glu Arg Ala Asp Arg Leu Arg Ser
305                 310                 315                 320

Tyr Ala Ser (2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO: 5:

AAGTTCAGCA CSTACGCSAC STGGTGGATC                                              30

(2) INFORMATION FOR SEQ ID NO: 6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO: 6:

CTTSGCCTCG ATCTGSCGGA TSCGCTC                                                 27

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO: 7:

TTCCATGGGG TATGTGGCAG CGACC                                                   25
```

(2) INFORMATION FOR SEQ ID NO: 8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "PCR primer"

(xi) SEQUENCE DESCRIPTION: SEQ ID NO: 8:

```
GTACAGGCCA GCCTCGATCC GCTTGGC                              27
```

(2) INFORMATION FOR SEQ ID NO: 9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "PCR primer"

(xi) SEQUENCE DESCRIPTION: SEQ ID NO: 9:

```
TTTCATGGCC GATGCACCCA CAAGGGCC                             28
```

(2) INFORMATION FOR SEQ ID NO: 10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "PCR primer"

(xi) SEQUENCE DESCRIPTION: SEQ ID NO: 10:

```
CTTGAATTCA GCTGGCGTAC GACCGCA                              27
```

(2) INFORMATION FOR SEQ ID NO: 11:

(i) SEQUENCE CHARACTERISTICS:
        (A) LENGTH: 7 amino acids
        (B) TYPE: amino acid
        (D) TOPOLOGY: linear     (ii) MOLECULE TYPE: protein     (xi) SEQUENCE DESCRIPTION: SEQ ID NO: 11:

```
Met Gly Tyr Val Ala Ala Thr
1               5
```

(2) INFORMATION FOR SEQ ID NO: 12:

(i) SEQUENCE CHARACTERISTICS:
        (A) LENGTH: 8 amino acids
        (B) TYPE: amino acid
        (D) TOPOLOGY: linear     (ii) MOLECULE TYPE: protein     (xi) SEQUENCE DESCRIPTION: SEQ ID NO: 12:

```
Met Ala Asp Ala Pro Thr Arg Ala
1               5
```